United States Patent

Meier et al.

[11] Patent Number: 5,987,993
[45] Date of Patent: Nov. 23, 1999

[54] TEST APPARATUS AND METHOD FOR NONDESTRUCTIVE MATERIAL TESTING

[75] Inventors: Rainer Meier, Erlangen; Dieter Lingenberg, Frankfurt, both of Germany

[73] Assignee: Siemens Aktiengesellschaft, Munich, Germany

[21] Appl. No.: 08/893,824

[22] Filed: Jul. 11, 1997

[30] Foreign Application Priority Data

Jul. 11, 1996 [DE] Germany .......................... 196 28 028

[51] Int. Cl.⁶ .......................... G01N 29/06; G01N 29/24
[52] U.S. Cl. ........................................................ 73/643
[58] Field of Search .......................... 73/643, 632, 641, 73/578; 324/221, 222

[56] References Cited

U.S. PATENT DOCUMENTS

| | | | |
|---|---|---|---|
| 3,697,867 | 10/1972 | Kleesattel | 73/643 |
| 4,312,231 | 1/1982 | Kawashima et al. | 73/643 |
| 4,320,661 | 3/1982 | Peterson et al. | 73/643 |
| 4,395,913 | 8/1983 | Peterson | 73/643 |
| 4,450,725 | 5/1984 | Yamaguchi et al. | 73/643 |
| 4,466,287 | 8/1984 | Repplinger et al. | 73/643 |
| 4,471,658 | 9/1984 | Morimoto | 73/643 |
| 5,421,203 | 6/1995 | Graff et al. | 73/643 |

FOREIGN PATENT DOCUMENTS

| | | |
|---|---|---|
| 0579255B1 | 1/1994 | European Pat. Off. . |
| 2726827 | 2/1978 | Germany . |
| 3511768A1 | 10/1986 | Germany . |
| 4204643C1 | 5/1993 | Germany . |

*Primary Examiner*—Hezron Williams
*Assistant Examiner*—Rose M. Miller
*Attorney, Agent, or Firm*—Herbert L. Lerner; Laurence A. Greenberg

[57] ABSTRACT

The test apparatus for nondestructive material testing using electrodynamically generated ultrasonic waves. A high-frequency coil assembly has an end face perpendicular to a surface of the workpiece and it is disposed between at least two magnets. Efficient generation and reception of ultrasonic waves is thereby assured.

14 Claims, 1 Drawing Sheet

TEST APPARATUS AND METHOD FOR NONDESTRUCTIVE MATERIAL TESTING

BACKGROUND OF THE INVENTION

1. Field of the Invention

The invention relates to a test apparatus and a method for nondestructive material testing using electrodynamically generated ultrasonic waves.

Ultrasonic testing is a method of nondestructive material testing using ultrasound to detect cracks, inclusions, inhomogeneities, and other flaws. The ultrasound is generated piezoelectrically or electrodynamically, for example.

2. Description of the Related Art

In electrodynamic ultrasound generation, the ultrasound is generated directly in the test specimen, so that a coupling medium is not needed. The creation of the ultrasonic oscillations can be ascribed to the interaction of high-frequency eddy currents with a magnetic field. The eddy currents are generated for instance by a high-frequency coil assembly that is placed in the vicinity of the surface of the workpiece. Lorentz forces are created by means of a simultaneously operative magnetic field which produce sound waves in the workpiece. Depending on the orientation of the magnetic field and the eddy-current-generating coil relative to one another, longitudinal waves and arbitrarily polarized transverse waves can be induced. In the longitudinal wave, the direction of propagation and vibration are identical, while conversely in the case of the transverse wave the direction of the vibration is perpendicular to the direction of propagation. The transverse wave is also known as a thrust or shear wave which propagates only in solid media.

If the direction of polarization is located in the plane defined by the surface normal of the workpiece and the direction of propagation of the ultrasound, then one speaks of vertically polarized transverse waves. Conversely, if the direction of polarization is perpendicular to that plane, one speaks of horizontally polarized transverse waves. For use in the testing industry, horizontally polarized transverse waves can be generated only by electrodynamic excitation.

With electrodynamic ultrasound generation, it is possible to test the workpiece at temperatures up to about 1000K.

German Patent DE 42 04 643 discloses a test apparatus with a perpendicularly oriented permanent magnet, whose orientation changes in checkerboard fashion. The direction between the north and south poles of the permanent magnet is defined as the orientation. In this apparatus, the high-frequency coil is disposed in meandering fashion between a surface of the workpiece and the permanent magnet. This test apparatus is very complicated and expensive to manufacture, since the transmitting or receiving coil in flat form must be wound very thinly. At the previously conventional testing frequencies of approximately 0.7 MHz, this can be achieved only at very major effort and expense. For testing thin-walled components and pipelines, however, frequencies between 1 and 2 MHz are usual. To achieve this, the permanent-magnet and high-frequency coil arrangements must be reduced in size in accordance with the frequency. This makes the replicable production of such test apparatuses very complicated and expensive.

European Patent Disclosure EP 0 579 255 discloses a further test apparatus, in which the eddy currents required to excite sound are induced via a magnet yoke that encloses the permanent magnets. The distance between the two pole pieces of the magnet yoke is undesirably great. Thus that test apparatus is highly dependent in its efficiency, with respect to sound excitation and sound reception, on the material to be tested. For instance, satisfactory results have thus far been unattainable with nonmagnetic components. Yet precisely in the case of nonmagnetic weld seams and mixed seams, the use of horizontally polarized waves, which can be generated practically only electrodynamically, is especially suitable because of the columnar crystals through which the ultrasonic transmission is to take place.

SUMMARY OF THE INVENTION

It is accordingly an object of the invention to provide a test apparatus and a method for nondestructive material testing, which overcomes the above-mentioned disadvantages of the heretofore-known devices and methods of this general type and which assures efficient generation and reception of ultrasonic waves and, furthermore, which is economical to manufacture.

With the foregoing and other objects in view there is provided, in accordance with the invention, a test apparatus for nondestructive testing of a workpiece, comprising: two mutually spaced-apart magnets and a high-frequency coil assembly electrodynamically generating ultrasonic waves disposed between the magnets, the coil assembly having an end face extending perpendicularly to a surface of the workpiece.

In other words, the above objects are satisfied by a test apparatus for nondestructive material testing using electrodynamically generated ultrasonic waves, wherein a high-frequency coil assembly with an end face perpendicular to the surface of the workpiece is disposed between at least two magnets.

With this test apparatus, efficient excitation and reception of electrodynamically generated ultrasonic waves is assured, both in ferromagnetic and nonmagnetic workpieces. The high-frequency coil is coupled directly to the workpiece to be tested, via a thin protective layer. Due to the fact that the high-frequency coil is disposed between the magnets, the test system is simplified, with regard to the prior art, in terms of manufacture and assemblage. Thus the magnets and the high-frequency coil can be disposed side by side, while conversely in the apparatuses known from the prior art, a complicated arrangement of the components one above the other is accomplished. As a result, the manufacturing costs for the novel apparatus are considerably reduced.

In accordance with an added feature of the invention the magnets and the high-frequency coil assembly each have coupling faces which lie substantially in a common plane, and the magnets are oriented perpendicular to the surface of the workpiece.

In accordance with an additional feature of the invention, a coil core is disposed in the longitudinal axis of the high-frequency coil. In particular, the coil core is made from soft magnetic material. A soft magnetic material is an easily magnetized and demagnetizable ferromagnetic material. Given a suitable choice of the material, for instance for the suitable frequency range of the ultrasonic waves, a significant signal amplification of the transverse ultrasonic waves to be received is achieved as a result of the permeability of the coil core.

In accordance with another feature of the invention, the coil core is a cylinder or a parallelepiped. These are relatively simple shapes, and they allow a simple embodiment of the test apparatus to be realized.

In a further feature, the winding of the high-frequency coil assembly is disposed tightly on the coil core, i.e., the coil is tightly wound on the core. Because the winding of the high-frequency coil assembly can be wound on the coil core in a defined way, defined coil data are obtained. This is a further improvement with regard to the test apparatuses known from the prior art, where the high-frequency coil is for instance disposed in meandering fashion below the permanent magnets.

The replicability of the properties of the test apparatus is thus substantially improved. The effect of the material of the workpiece on the electrical properties of the test apparatus is minimized. Typically, the high-frequency coil assembly is supplemented with a capacitor to make an oscillating circuit, whose resonant frequency is in the vicinity of the test frequency. This has the effect that the resulting circuit impedance is reduced approximately to the ohmic portion and the signal excitation is thus improved. In this version of the high-frequency coil, the oscillating circuit tuning is very stable, and both the resonant frequency and the damping by the workpiece are only minimally affected.

In accordance with two concomitant features of the invention, the magnets may be permanent magnets or electromagnets.

Other features which are considered as characteristic for the invention are set forth in the appended claims.

Although the invention is illustrated and described herein as embodied in a test apparatus and a method for nondestructive material testing, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
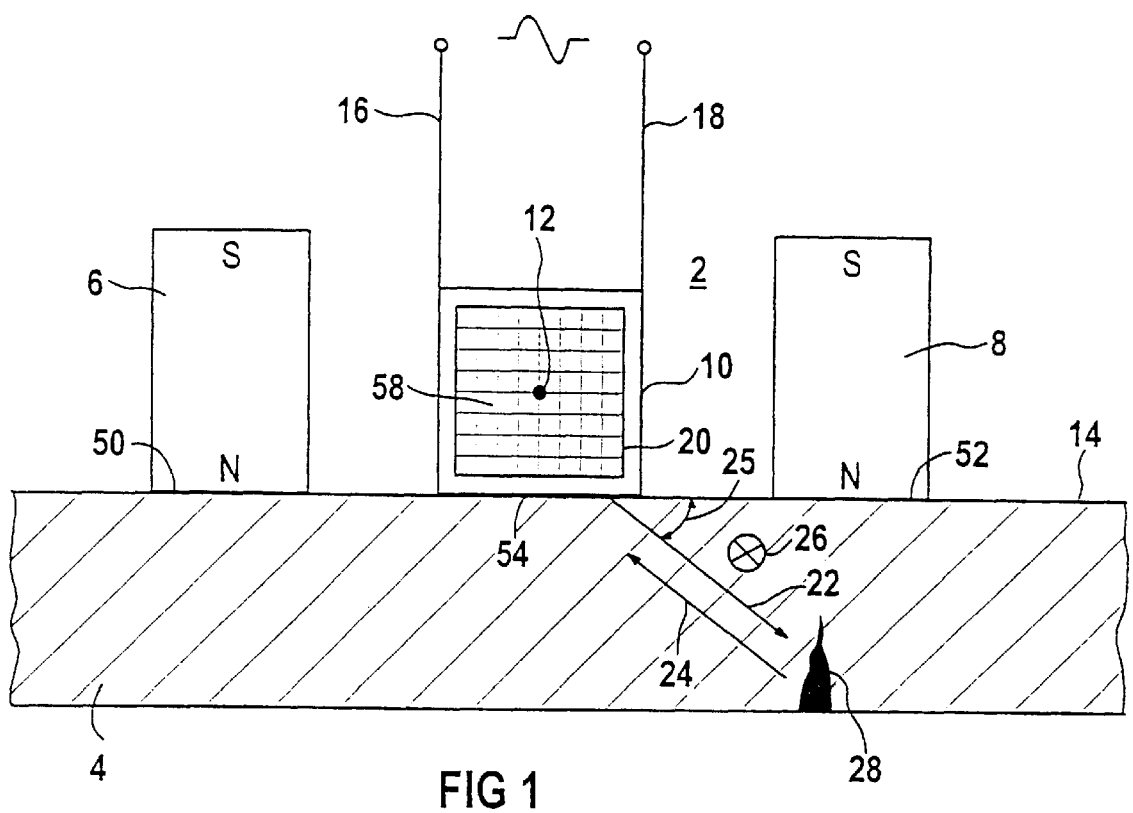
FIG. 1 is a schematic partial side view of an assembly according to the invention.

Referring now to the figures of the drawing in detail, and first, particularly, to FIG. 1 thereof, a test apparatus 2 for nondestructive material testing includes two permanent magnets 6 and 8 and one high-frequency coil assembly 10. The high-frequency coil assembly 10 is coupled to the workpiece 4 between the permanent magnets 6 and 8, with its longitudinal axis 12 parallel to one surface 14 of the workpiece 4. The coupling faces 50, 52, 54 of the permanent magnets 6, 8 and of the high-frequency coil assembly 10 are disposed in one plane. The longitudinal axis 12 is oriented perpendicular to the plane of the drawing, so that one end face 58 (and thus also a cross-sectional face) of the high-frequency coil assembly 10 10 is located in the plane of the drawing and perpendicular to the surface 14 of the workpiece 4.

This test apparatus 2 assures efficient excitation and reception of electrodynamically generated transverse ultrasonic waves 22, 24. The ultrasonic waves 22, 24 propagate at the angle of incidence 25 in the workpiece 4 and are suitable for investigating both ferromagnetic and nonmagnetic workpieces 4.

The high-frequency coil assembly 10 is coupled indirectly to the workpiece 4 to be tested via a thin guard layer, which is not shown in any greater detail in the figure. The test apparatus 2 is quite simple in its manufacture and assembly because the high-frequency coil assembly 10 is disposed between the two permanent magnets 6, 8.

The high-frequency coil assembly 10 is supplied with a high-frequency electrical alternating current via the lines 16, 18.

A coil core 20 of soft magnetic material is disposed in the longitudinal axis 12 of the high-frequency coil assembly 10. Given a suitable selection of material, for instance for the suitable frequency range of the transverse ultrasonic waves 22, 24, a significant signal amplification of the ultrasonic waves 22, 24 to be received is achieved by the permeability of the coil core 20. The coil core 20 has the shape of a parallelepiped. However, a cylinder may also be used as the coil core 20.

The winding of the high-frequency coil assembly 10 is disposed tightly on the coil core 20. This substantially improves the replicability of the characteristic properties of the test apparatus 2.

Particles in the workpiece 4—in the case of the transverse ultrasonic waves 22, 24—are deflected perpendicularly to the direction of propagation, as indicated by the arrow 26 (into the plane of the figure). In the pulsed echo method described, the ultrasonic wave 22 generated by the test apparatus 2 is reflected at an inhomogeneity 28. The reflected ultrasonic wave 22 is received by the test apparatus 2, which in the meantime has been switched over from being an ultrasound generator to being an ultrasound receiver.

In an alternative embodiment which is not illustrated in detail, the high-frequency coil may be rotated 90° parallel to the surface 14, so that the permanent magnets 6, 8 are disposed on the face ends 58, 60 of the high-frequency coil assembly 10. As a result, the direction of propagation of the ultrasonic waves 22 is perpendicular to the surface 14, or in other words is at the angle of incidence 25 of 90°. The permanent magnets 6, 8 are oriented perpendicularly to the surface 14 of the workpiece 4. They can also be electromagnets.

Figure 2:
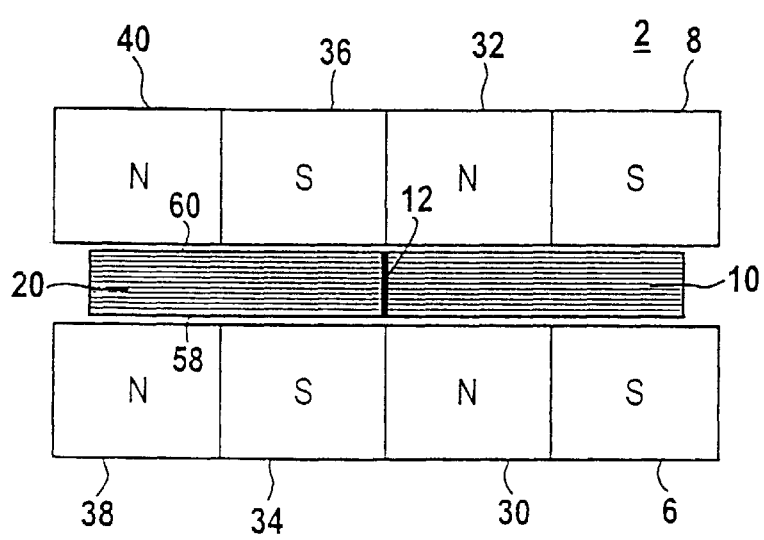
FIG. 2 is a plan view of a further test apparatus.

FIG. 2 shows a further test apparatus 2 in a plan view. In contrast to FIG. 1, a plurality of permanent magnets 6, 8, and 30–40 are provided here.

The permanent magnets 6, 30, 34, 38 on the one hand and 8, 32, 36, 40 on the other are each disposed in succession on an axis at right angles to the longitudinal axis 12 of the high-frequency coil assembly 10 on the respective end face 58 and 60. The orientation of the permanent magnets 6, 8, 30–40 is antiparallel to one another. In other words, a magnetic south pole has an adjacent north pole, and vice versa.

In an alternative embodiment which is not illustrated in detail, the orientations of the permanent magnets 6, 8, 30–40 are parallel to one another. In other words, a south pole for instance has a south pole as its neighbor.

A plurality of these test apparatus 2 shown in FIGS. 1 and 2 can be combined in a suitable way to make a test head. In other words, a plurality of these test apparatuses 2 can be disposed in line with one another or side by side. Individual test apparatus 2 of the test head can be driven (triggered) in a suitable way in order to obtain a predetermined ultrasonic wave profile.

We claim:

1. A test apparatus for nondestructive testing of a workpiece, comprising:

at least two mutually spaced-apart magnets with a gap therebetween; and a high-frequency coil assembly electrodynamically generating ultrasonic waves, said high-frequency coil assembly being disposed in the gap between said magnets and having an end face extending perpendicularly to a surface of the workpiece.

2. The test apparatus according to claim 1, wherein said magnets and said high-frequency coil assembly each have coupling faces, said coupling faces of said magnets and of said high-frequency coil assembly being disposed substantially in a common plane, and wherein said magnets are oriented perpendicular to the surface of the workpiece.

3. The test apparatus according to claim 1, wherein said high-frequency coil assembly has a longitudinal axis and a coil core disposed along said longitudinal axis.

4. The test apparatus according to claim 3, wherein said coil core is formed of soft magnetic material.

5. The test apparatus according to claim 3, wherein said coil core is a cylinder.

6. The test apparatus according to claim 5, wherein said coil core is formed of soft magnetic material.

7. The test apparatus according to claim 3, wherein said coil core is a parallelepiped.

8. The test apparatus according to claim 7, wherein said coil core is formed of soft magnetic material.

9. The test apparatus according to claim 3, wherein said high-frequency coil assembly has a winding wound tightly on said coil core.

10. The test apparatus according to claim 1, wherein said high-frequency coil assembly is formed with end faces and said magnets are disposed on said end faces of said high-frequency coil assembly.

11. The test apparatus according to claim 1, wherein said high-frequency coil assembly is formed with end faces, and said magnets are parallel to said end faces and aligned one behind the other in alternating magnetic orientation.

12. The test apparatus according to claim 1, wherein said magnets are permanent magnets.

13. The test apparatus according to claim 1, wherein said magnets are electromagnets.

14. A method of nondestructive testing of a workpiece with a surface, which comprises:

placing a high-frequency coil assembly in a gap between at least two mutually spaced-apart magnets, and coupling the high-frequency coil assembly to a workpiece, with an end face of the coil assembly extending perpendicularly to a surface of the workpiece; and electrodynamically generating ultrasonic waves with the high-frequency coil assembly.

\* \* \* \* \*